United States Patent [19]

Gallop et al.

[11] Patent Number: 4,759,361
[45] Date of Patent: Jul. 26, 1988

[54] TELESCOPIC ADJUSTMENT ASSEMBLY FOR HEAD POSITIONING MEANS IN A CEPHALOSTAT

[75] Inventors: James L. Gallop, Wheaton; Andrew J. Majka, Chicago, both of Ill.

[73] Assignee: B. F. Wehmer Co., Inc., Franklin Park, Ill.

[21] Appl. No.: 897,606

[22] Filed: Aug. 18, 1986

[51] Int. Cl.$^4$ ............................................. G03B 41/16
[52] U.S. Cl. ............................... 128/303 B; 378/174; 378/163
[58] Field of Search ............... 128/303 B, 653; 378/20, 378/79, 81, 177, 178, 179, 180, 208, 162, 163, 174

[56] References Cited

U.S. PATENT DOCUMENTS

| | | |
|---|---|---|
| 2,032,833 | 3/1936 | Broadbent . |
| 2,254,544 | 9/1941 | Plotz et al. . |
| 2,264,410 | 12/1941 | Schier . |
| 2,717,314 | 9/1955 | Delk, Sr. . |
| 2,846,587 | 8/1958 | Thurow . |
| 3,072,788 | 1/1963 | Oller . |
| 3,154,683 | 10/1964 | Blair . |
| 3,293,430 | 12/1966 | Wustner . |
| 3,364,352 | 1/1968 | Fry et al. . |
| 3,514,606 | 5/1970 | Rabey . |
| 3,530,293 | 9/1970 | Wehmer . |
| 3,626,186 | 12/1971 | Allard . |
| 3,633,028 | 1/1972 | Marino . |
| 3,704,707 | 12/1972 | Halloran . |
| 3,737,660 | 6/1973 | Ando et al. . |
| 3,790,803 | 2/1974 | Phillips . |
| 3,916,207 | 10/1975 | Reed . |
| 4,088,893 | 5/1978 | Schroeder . |
| 4,144,460 | 3/1979 | Norman . |
| 4,145,611 | 3/1979 | Valila . |
| 4,229,656 | 10/1980 | Iversen et al. . |
| 4,256,112 | 3/1981 | Kopf et al. . |
| 4,341,220 | 7/1982 | Perry . |
| 4,400,826 | 8/1983 | Preti et al. . |
| 4,566,444 | 1/1986 | Spolyar ............... 128/303 B |
| 4,579,117 | 4/1986 | Spolyar ............... 128/303 B |

OTHER PUBLICATIONS

Brochure Entitled "The Axialtome" (two pages) by Wilson Radiographic Systems, Inc.

Primary Examiner—Edward M. Coven
Attorney, Agent, or Firm—Lee & Smith

[57] ABSTRACT

A telescoping adjustment assembly for head positioning means used in a cephalostat. The assembly having sleeves retractably engaged by slide arms, the outward ends of the arms and sleeves carrying brackets for supporting the head positioning means. Substantially no portions of the slide arms or sleeves extend outwardly of the brackets so that the assembly is compact and allows use with tomographic x-ray equipment so that the support portions for the brackets do not shadow the radiograph or provide physical impediments to the rotation of a co-axial x-ray tube and film holder. The assembly is further useful for both fixed-type cephalostats, and angularly adjustable cephalostats of the type wherein lateral and anterior, posterior, and oblique cephalometric studies may be made, wherein the stable, compact adjustment assembly provides very accurate positioning of the cranium, dentition, TMJ, etc.

36 Claims, 4 Drawing Sheets

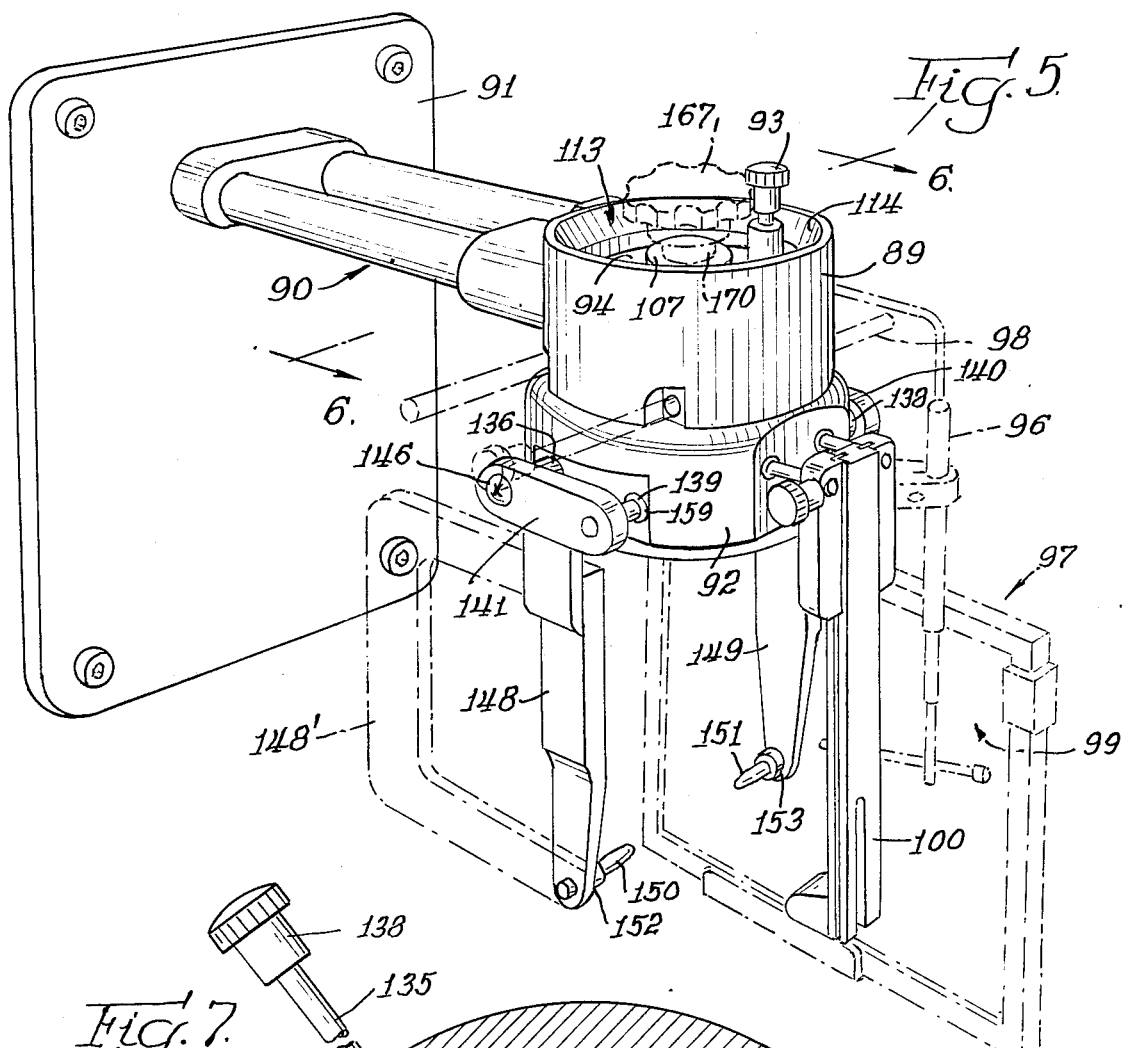
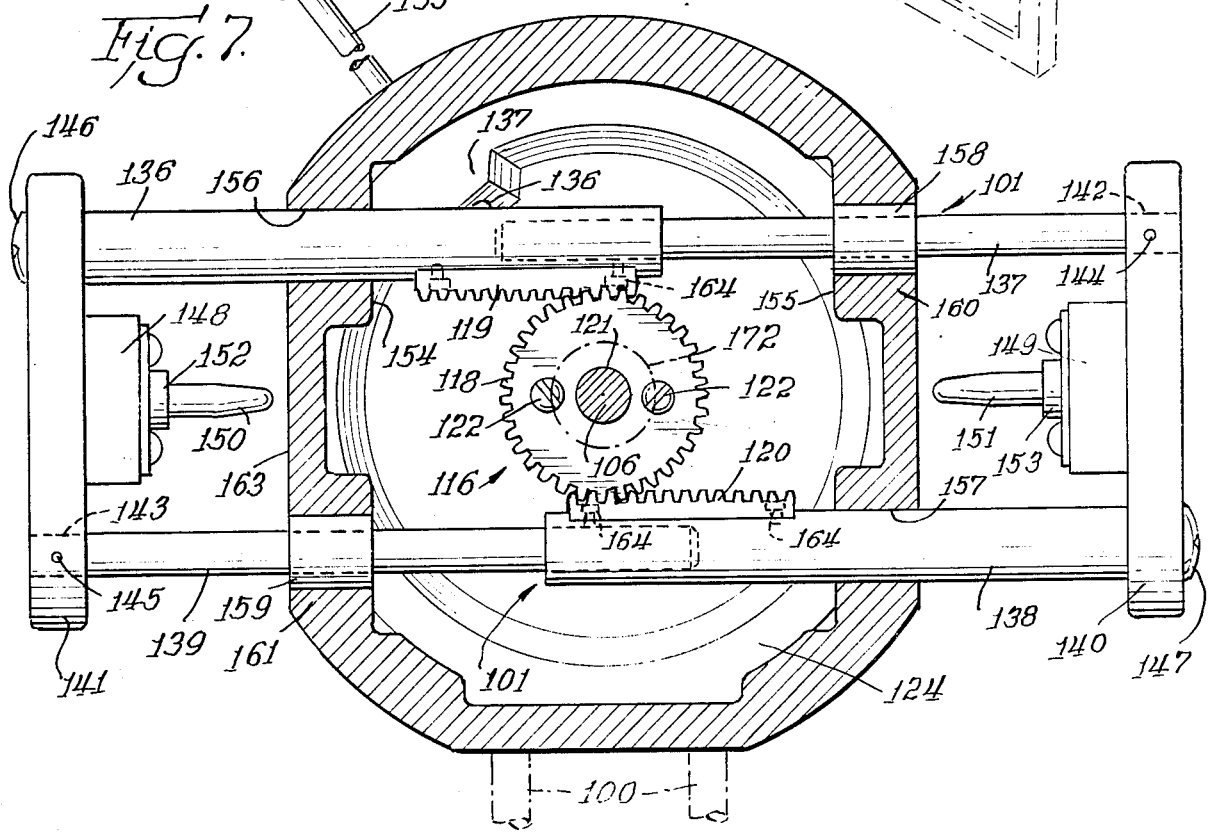

TELESCOPIC ADJUSTMENT ASSEMBLY FOR HEAD POSITIONING MEANS IN A CEPHALOSTAT

BACKGROUND OF THE INVENTION

The present invention relates to an adjustment assembly for head positioning means in a cephalostat used for positioning the head while taking radiographs, particuarly in cephalometric study. The invention has particular suitability for those cephalostat devices used to obtain tomograms of the dentition. The adjustment assembly provides a very close, exact and stable adjustment capability while importantly eliminating support arms and rods from projecting outwardly of the cephalostat to thereby grant more usable space around the device for revolving an x-ray source and co-axial film holder and further eliminating shadows on the radiograph, otherwise caused by protruding adjustment and support arm components of known positioners.

Cephalostats typically provide head positioning means including earposts that carry ear pins or plugs for insertion into the ear canals. Thereby the porion axis is aligned between the ear pins so that accurate measurements and permanent radiographs for cephalometric studies may be generated from patients at different periods of time during growth or orthodontia with the desirable capability of allowing the practitioner to make exact comparative diagnoses and study, and the clear advantages obtained thereby for effective treatment.

Cephalostats are useful for tomographic type of radiographic series wherein an x-ray source and film holder revolve about the patient's head in a selected series of revolutions. Additionally, cephalostats may be used in more conventional x-ray tube alignments in which the x-ray tube is fixed for a particular roentgenograph and wherein, in sequence, the patient's head may be positioned laterally, obliquely, anteriorly or posteriorly with regard to the x-ray tube and to an x-ray film holder disposed in alignment with the axis of the x-ray tube whereby front, side, back and angular radiographs may be taken so that cephalometric studies may be made and compared with subsequent or earlier radiographs for study.

For both tomographic and fixed-type x-ray tube techniques, involving lateral, posterior, anterior and oblique radiography, cephalostats have been sought which include head positioning means having earposts and earplug means that are compact, sturdy, tightly and smooth fitting with the cephalostat housing, wherein the positioning means are adjustable to move the earplugs inwardly of the ear canal, and outwardly therefrom for quick, and efficient and exact positioning of the patient's head. The positioning primarily involves locating the porion axis and Frankfort plane in standard relationships to the film for radiographic studies, particularly those involved with study of the dentition and temporal-mandibular joint (TMJ). An adjustable assembly would be desirable that would offer a compact arrangement allowing x-ray equipment and film holders, as well as other positioning means such as nasion positioner, orbitali locator, and forehead and chin positioners, to be utilized without protuberances extending outwardly of the cephalostat housing. Furthermore, eliminating such protuberances would be helpful to prevent corresponding shadows or blocked-out zones on the radiographs from occurring. Thus, particularly for tomographic techniques, a non-protruding, adjustable head positioning means would be highly desirable to increase the arc within which the x-ray tube and axially aligned film holder might move. Additionally, this would also permit a closer positioning of the x-ray tube and film holder to the patient's head as might be required, as well as allowing the carrying arm and support means for the x-ray tube and film holder to have greater spatial freedom of movement with respect to the cephalostat by the elimination of protruding adjustment arm means and the like.

SUMMARY OF THE INVENTION

It is accordingly a primary object of the invention to provide an adjustment assembly for the head positioning means in a cephalostat for use with either tomographic techniques, or fixed tube radiographic procedures, of the conventional type utilizing lateral, anterior, posterior, or oblique dispositions of the cranium or dentition relative to the x-ray film.

It is a main goal of the invention to provide an adjustment means that offers a compact arrangement with a cephalostat housing whereby to eliminate lateral protuberances of the adjustment means, such as the typical movable arms for carrying earpost and earplug means, so as to provide spatial freedom for the x-ray tube and film holder to be stationed therearound and to attain the elimination of shadows on the radiograph.

It is further an object of the invention to provide a telescoping adjustment assembly wherein carrier supports for the earposts reciprocally telescope and retract in a compact arrangement. It is further a goal of the invention to provide for such a compact arrangement having a very sturdy, close-sliding and stable support provided in a telescoping arrangement by virtue of the capability of rigidlly connecting the carrier arms, or rods, to brackets that carry the earposts. It is therefore a concomitant objective to eliminate the loose "play" that normally occurs in prior art assemblies where the slide arms or rods of the adjustment assembly move, or slide, through the bracket, or a bushing therein, which inherently has created slack and looseness causing unwanted rattling, insecurity, and sloppy control movement. A sliding telescope arrangement for sleeves and slide arms carrying the earposts desirably tightly nest together and eliminate such slack or "play" by being rigidly affixed to the earpost bracket or carrier means at one end and telescoping in tightly fitting copperation with a reciprocating arm or ide means at the other.

A further object of the invention is to provide an adjustment assembly for the head positioning means in a cephalostat for which the assembly may be used in housing arrangments by employing a pivot arm adjustment which preferably moves a rotatable circular member at one side of a cephalostat housing, or alternatively wherein a knob adjustment means is located externally of the cephalostat housing wherein the practitioner may either simply turn a pivot arm or an adjustment knob and thereby retract or extend the earposts laterally of the cephalostat.

Moreover, it is also an object of the invention to provide for an arm adjustment assembly wherein the pivot arm may be disposed in a horizontal plane preferably behind the cephalostat housing, or wherein the pivot arm may be inclined upwardly or downwardly from the housing for ease of access and to meet spatial requirements. It is an alternative object of the invention to provide an adjustment assembly wherein a pinion is rotatable either in association with a rotatable shaft, or rotatable plate along a cephalostat housing, for oppositely moving gear racks mounted to a pair of similarly reciprocating sleeve means whereby the sleeve means move the earposts and also associate with insertable/retractable slide arms therein for reciprocal action having the sleeve means and slide arms each oppositely mounted at an opposing bracket means. Thereby, each earpost bracket is supported on a sleeve means and a slide arm means which opposingly and telescopingly align in correspondence with sleeve means and slide arm means supported at the other bracket means. Gear rack means extend along oppositely directed inward surfaces of the sleeve means and are gear-tooth engaged with a rotatable pinion, preferably interiorly of a cephalostat housing. The pinion desirably may be driven by a shaft connected to an outward extending turnable knob means, or optionally wherein a rotatable plate means is rigidly associated with the pinion and is arranged with lever or pivot arm means outwardly of the cephalostat housing for the turning manual adjustment thereof.

It is also an object of the invention to provide a telescoping earpost adjustment assembly for a cephalostat wherein the cephalostat includes nestable means along the cephalostat body or housing whereby the earposts and the earpost-carrying brackets may be compactly accommodated against the cephalostat housing whereby to provide for a very efficiently sized arrangement with the cephalostat enabling other x-ray equipment, such as a rotating x-ray tube and film holder, to move thereabout for versatility and exactitude to be had in radiography procedures. Additionally, this compact arrangement allows implementation of variously shaped earpost designs to suit particular spacing and positioning needs and wherein they may be of a material that does not shadow a radiograph.

The invention further prevents gear and rack disengagement by provided stop means for the gear and rack, whereby to also prevent unwanted disengagement of the slide arms from the sleeve means.

The telescoping adjustment assembly for the head positioning means is capable of utilization in a cephalostat of the simple fixed housing variety of or the type wherein plural housings are relatively rotatable, usually having one rigidly mounted by support arms to a wall mounting unit, and further wherein a variety of rotation adjustment means for oblique radiography may be used in conjunction with controlling the relative rotation of the housings. Further, a multi-housing cephalostat may also be accommodated by the telescoping adjustment assembly wherein a bottom rotatable plate is rotatably associated with a central shaft having a portion thereon rigidly affixed to one housing portion and wherein the bottom plate has an axial bore that is freely turnable about the plate wherein upon the association of a pivot or control arm, the rotatable bottom plate is movable. Thereby, it is an object of the invention to advantageously utilize said rotatable shaft by affixing thereto the gear pinion whereby rotation of the plate correspondingly rotates the pinion to drivingly reciprocate the gear racks and the associating sleeve means and slide arm means of the assembly. It will be understood that the invention comprises two pair of slide arm means and sleeve means reciprocally driven by a rotatable pinion engaged with gear racks mountably associated with each pair of slide arm means and sleeve means whereby to drive them in opposite directions upon rotation of the pinion. Further, the slide arm means and sleeve means have inner ends to be arranged interiorly of a cephalostat housing and opposite housing-outward ends preferably being affixed to brackets, or optionally being directly affixed to the earposts, whereby solid, tight movement is achieved without wobble, "play" or slack among the earposts, or brackets, and the slide arm means and sleeve means. The gear pinion may be driven by a shaft extending outwardly of the housing whereby a knob, or the like, attached thereto may be rotated to turn the gear pinion and thereby reciprocally move the two pair of slide arm means and sleeve means. Alternatively, plate means, preferably arranged, in a covering fashion for a cephalostat housing, may be rotatably arranged on a shaft or the like, that is otherwise affixed to another portion of the housing, wherein the gear pinion is affixed to the rotatable plate means whereby rotation thereof turns the gear pinion for the reciprocal driving of said gear racks. Outwardly extending lever or pivot arm means may be employed for the practitioner to easily grasp and move to thereby rotate the pinion, move the gear racks, and reciprocally move the earposts and associated earplugs toward or away from the patient's head.

In preferred form, the pair of earposts carried outwardly of the cephalostat housing are moved in equal distances away from or toward the cephalostat housing whereby the mid-point distance between the earplugs is preferably directly below the cephalostat housing in order that the mid-sagital of the head may be repetitively positioned in the same alignment below the cephalostat housing in order to obtain a consistent series of radiographs over time with the patient's dentition, TMJ, etc., always located virtually in the same arrangement relative to the film. Thereby, once the practitioner places the x-ray tube and x-ray film in the same relationship to the mid-sagital, with the Frankfort plane and porion axis positioned as desired, comparative radiographs may be obtained to determine a patient's progress for orthodontia, or for the monitoring of other physiological changes and the like, as would be understood.

Further, means are provided whereby upon the utilization of a rotatable shaft for driving the pinion, axial stop means may be employed so that the shaft cannot be moved upwardly or downwardly to dislocate the pinion from the gear racks. Therefore, axial limit stops may be employed in this regard to prevent dis-engagement of the gear pinion and gear rack assembly.

Preferably, the invention further includes plastic or wood earposts and earplugs which do not shadow the x-ray and further may be formed in bowed, curved, U-shaped, double-bent configurations, and the like, to offset the earposts away from the path of the x-ray to achieve clear roentgenographs.

These and other objects of the invention will be found to be achieved upon review of the following drawings and specification for the preferred embodiment.

BRIEF DESCRIPTION OF THE DRAWINGS

FIG. 5 is perspective view of a rotatable type cephalostat wherein a fixed upper housing associates with a movable lower housing for lateral, anterior, posterior and angular radiography, and wherein the telescoping adjustment assembly for the earpost and ear plug means in this embodiment of the invention preferably includes a rearward extending pivoting arm for the adjustment, and wherein in phantom lines an alternative top knob adjustment alternative form of the invention is optionally usable in this rotatable type cephalostat;

FIG. 7 is a horizontal sectional view taken along lines 7—7 of FIG. 6 and showing the arrangement of the sleeve means and slide arm means, accommodated interiorly of the bottom housing of the cephalostat shown in FIG. 5, and drivingly engaged with a gear pinion and rack assembly wherein for the top knob adjustment alternative form of the invention a modification of the gear pinion is shown in phantom lines to include a hub portion to be affixed to an axial shaft for rotation thereof by means of the top knob adjustment capable of turning the axial shaft.

DESCRIPTION OF THE PREFERRED EMBODIMENT

Figure 1:
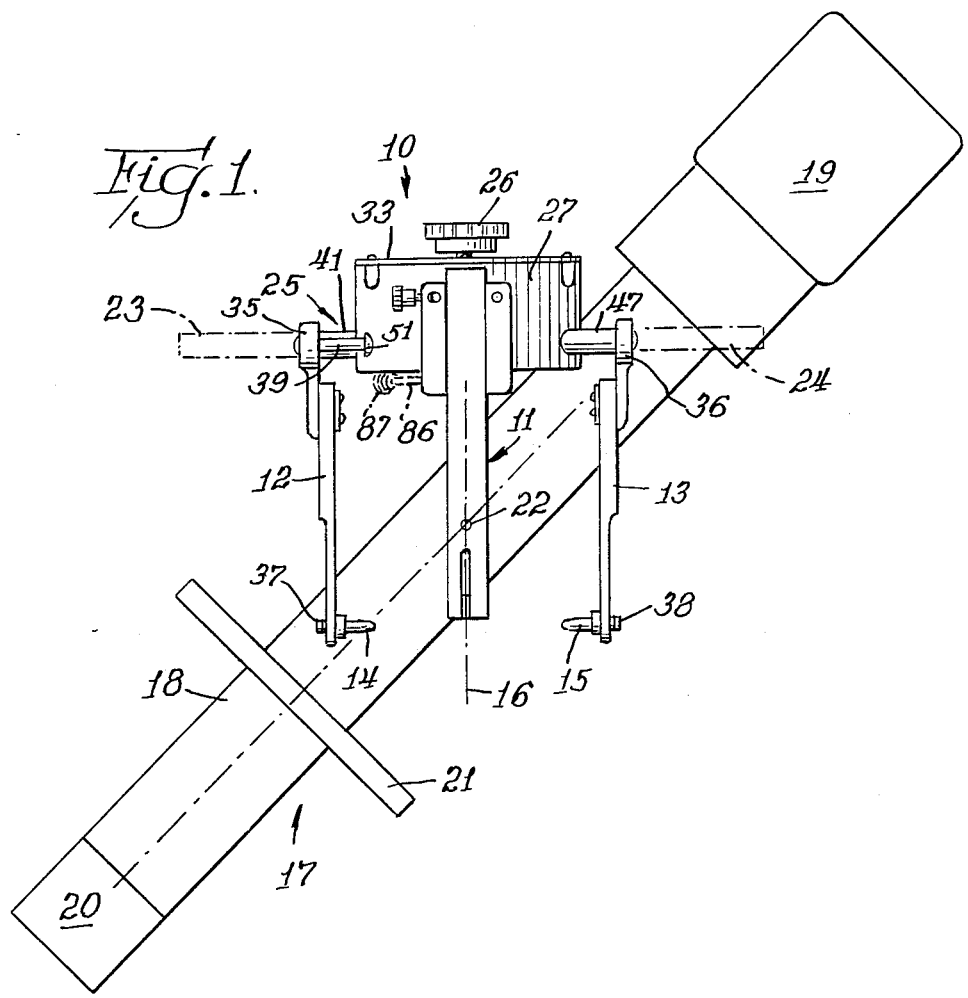
FIG. 1 is a front elevational view showing the telescoping adjustment assembly of the invention for head positioning earpost means and arranged in combination with a simple non-rotational cephalostat associated with a rotating x-ray tube and film holder for panoramic-tomographic-radiography, having nose positioning means for the nasion, and wherein the assembly is adjustable by means of a rotatable top adjustment knob, and also showing in broken lines the location of prior art extending slide arm means for a conventional head positioning earpost means assembly.
Figure 2:
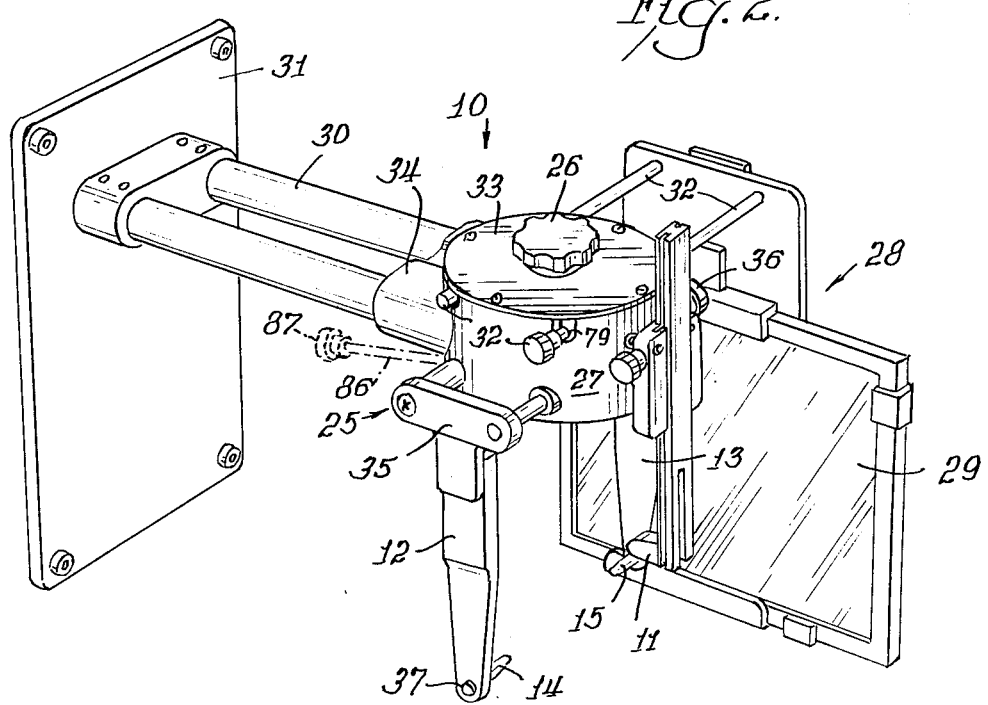
FIG. 2 is a perspective view of a cephalostat that is similar to that shown in FIG. 1 but for use with a laterally mounted static x-ray tube and a film cassette holder mounted thereon for lateral roentgenography and wherein the telescoping adjustment assembly for the unit is shown in solid lines with a top knob adjustment, and in phantom lines with a rearward pivot arm adjustment alternative form of the invention.

With reference first made to FIGS. 1 and 2, a cephalostat 10 is shown in a simplified version of this type of device which is non-rotational and wherein the patient's head is capable of being positioned below in one basic lateral orientation. The desired positioning of the head is in part accomplished by a conventional nasion positioning assembly 11 which may be of a known design in the art. Laterally of the patient's head, earposts 12 and 13 are movable to dispose ear plugs, or pins, 14, 15, respectively, into the ear canals of the patient. The relative motion of the earposts 12 and 13 should be very accurately controlled whereby the mid-sagital of the cranium is placed generally in the vertical plane 16 shown passing generally through the center of the nasion assembly 11. Thus, the ear plugs 14 and 15 preferably move at equi-distances at all times from the plane 16 to achieve this purpose.

In FIG. 1, a tomographic x-ray assembly 17 is arranged to pivot about the patient's head whereby, for example, tomograms of the dentition may be made for cephalometric study. It will be seen that at one end of an arm 18 resides an x-ray head or tube 19, and at the other end of the arm 18, a counterbalance 20 is provided. At a desired location along the arm 18, a film holder 21 is provided to be in axial alignment with the x-ray tube head 19 as would be understood. The assembly 17 rotates about a horizontal axis 22 at a pivoting means arranged therewith in an usual manner.

A major problem with the prior art that the present invention solves is exemplified by the broken lines of FIG. 1 wherein carrying arms, or supports, 23, 24 of the device are shown as they might conventionally extend laterally of the cephalostat 10 whereby to be in conflict with both the mechanical and the radiographic functions of the tomographic x-ray assembly 17. In solution thereof, an improved adjustment is provided at a telescoping adjustment assembly 25 in conformance with the invention. In this form of the preferred embodiment, the assembly 25 is operated by a manually adjustable top knob adjustment 26, which the physician or orthodontist may turn for controlling the spacing and position of the earposts 12 and 13. The adjustment assembly 25 mainly resides within, and is supported by, a housing 27 of the cephalostat 10. Instead of having the problem of protuberances, such as found with the conventional arms 23, 24, the telescoping adjustment assembly 25 provides movable sleeve means, and sliding, sleeve-insertable, arm means, which cooperate interiorly of the housing 27 whereby to eliminate lateral protrusions from extending outwardly no more than as necessary to connect to the earposts.

In FIG. 2, it will be observed that an arrangement for a conventional, lateral roentgenographic procedure is provided wherein a film cassette holder assembly 28 movably positions film 29 relative to the cephalostat 10. As in the device of FIG. 1, but not viewable therein, the housing 27 is supported by support arm means 30 which are attached to a wall plate support means 31 in a generally conventional assembly. An adjustment slide arm and knob means is shown generally at 32 for adjusting the lateral disposition of assembly 28. The top knob adjustment 26 emerges through a top plate 33 generally covering the housing 27 of the cephalostat 10. The housing 27 accommodates the sliding means 32 for the cassette assembly 28, the telescoping adjustment assembly 25, in addition to the adjustment means for the nasion positioner 11, as best shown with respect to FIG. 4, discussed hereinafter.

For the arrangement of the cephalostat 10 shown in FIG. 2, an x-ray tube would be disposed in alignment with the film 29 to the other side of the person's head so that a lateral radiograph may be made.

Figure 3:
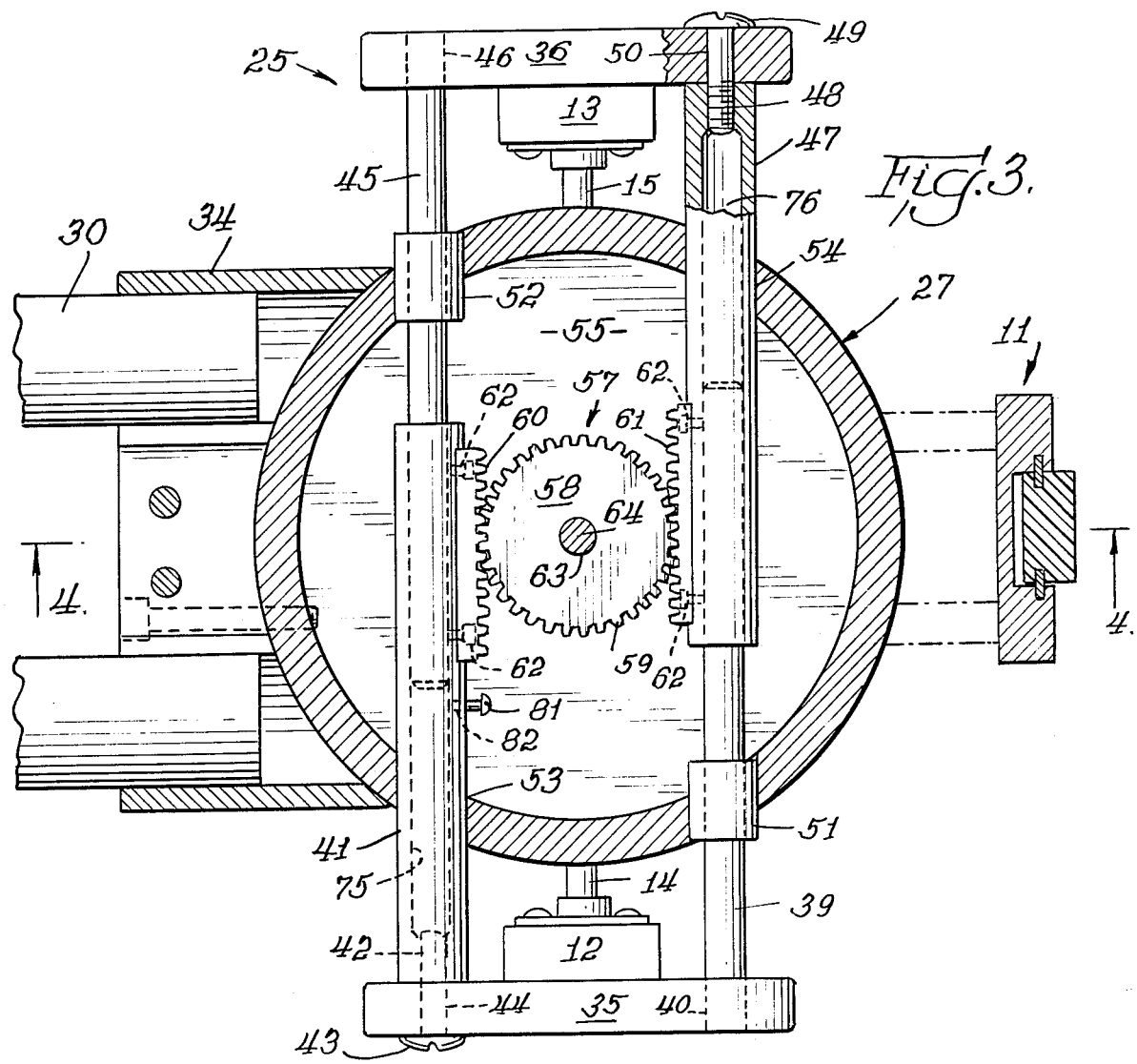
FIG. 3 is a horizontal sectional view taken through the cephalostat shown in FIGS. 1 or 2 wherein sleeve means and insertable slide arm means are shown in conjunction with a reciprocally driving gear and rack assembly therefor.
Figure 4:
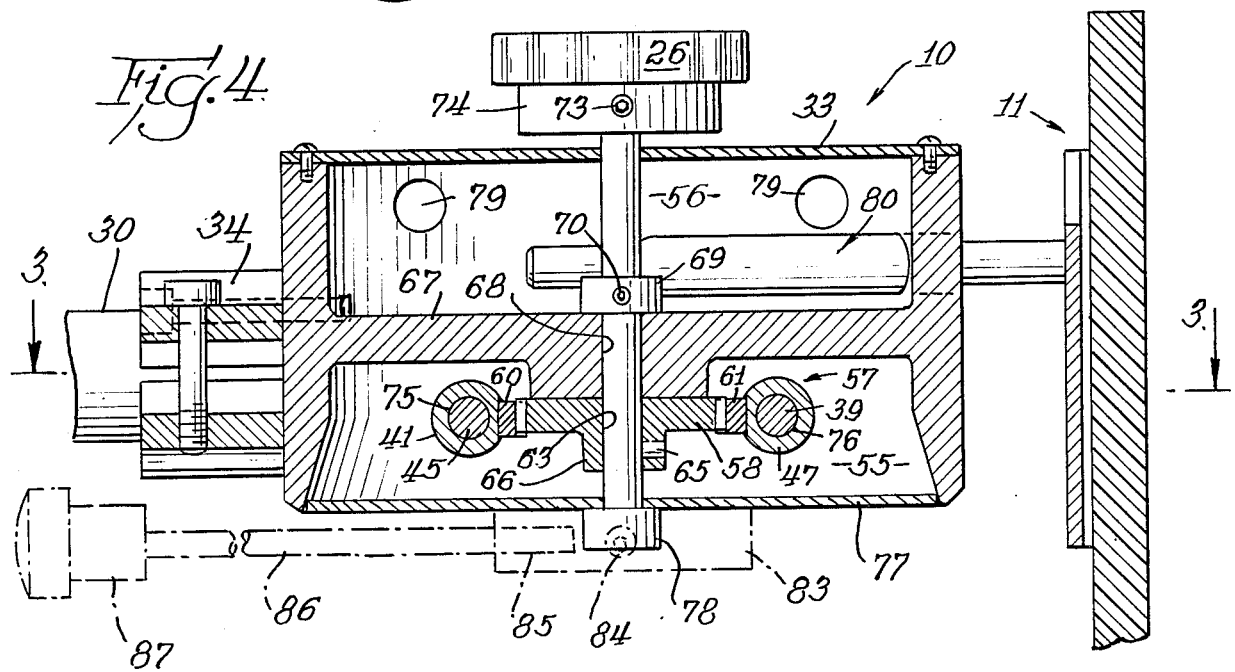
FIG. 4 is a vertical sectional view taken along line 4—4 of FIG. 3 looking in the direction of the arrows and showing the interior of the housing of the cephalostat accommodating the telescoping adjustment assembly having a top knob adjustment, and in phantom lines a bottom pivot arm adjustment alternative form of the invention.

With reference to the sectional views shown in FIGS. 3 and 4, greater detail of the inventive, telescoping adjustment assembly 25 is provided. Firstly, with respect to FIG. 3, it will be seen that the housing 27 is supported by the support arm means 30 which are in turn affixed to an integrally cast extension of the housing 27 having clamp-like receiving portions and tightening screws for the ends of the arms 30, and generally indicated at reference numeral 34. The assembly 25 includes a pair of opposing brackets 35 and 36 which may be made of metal, since, as shown in either of the arrangements of the cephalostat 10 in FIGS. 1 and 2, they will not impede, shadow or conflict with the x-ray taking function. It will be clear that the earposts 12 and 13, respectively, are dependingly supported by the brackets 35 and 36, and because they are disposed in the paths of the x-rays, the earposts 12 and 13 preferably are made of wood, plastic, or other suitable material that will not cloud the tomograph or radiograph. The earposts 12 and 13 may be attached to the brackets 35 and 36 by suitable mechanical fastening. In addition, flip-up earpost mechanisms, known in the art, may be provided at one or both of the bracket attachment locations.

At the lower ends of the earposts 12 and 13, the ear plugs 14 and 15 are provided for movement inwardly and outwardly of the patient's ear and are useful thereby to set the porion axis axially therebetween for the positioning of the cranium and dentition, as required. The ear plugs 14 and 15 are, in the preferred embodiment, affixed to the posts 12 and 13 by mechanical screw fasteners extending through a collar for clamping the ear plugs to the posts. These fasteners are preferably non-metallic for purposes of not clouding the x-ray. However, a metallic washer, or other element, may be provided at either of the attachment means 37 or 38, or at both, whereby to create a reference image point on an x-ray radiograph so that during cephalometric studies over a period of time such as in orthodontia, the relative change of teeth position to the reference point may be observed and measured for study of these spacing changes, or for growth changes, and the like. The brackets 35 and 36 move toward and away from the housing 11 and thereby carry the ear plugs 14 and 15 in a corresponding fashion whereby the distance between plug 14 and the plane 16 is always substantially equal to the distance between plug 15 and plane 16. The movement of the brackets 35 and 36 is controlled and provided by a telescoping sleeve and slide arm means of the telescoping assembly 25, as best viewed in FIGS. 3 and 4.

The assembly 25 is characterized by the reciprocating motion of opposing pairs of preferably solid slide arm means insertable into opposingly aligned generally tube-like receiving sleeve means. As will be noted, each bracket is supportably associated with the end of one of the solid slide arm means and an end of one of the sleeve means. Specifically, at bracket 35 a solid arm 39 has one end preferably pressfit into a bore 40 at generally one side of the bracket 35. At the other side of the bracket 35, a mainly hollow, or tubular, sleeve 41 includes a threaded axial end bore 42 through a solid outward end portion thereof which is thread-engaged by a mechanical screw fastener 43 extending through a smooth bore 44 of the bracket 35 for attachment of the sleeve 41 thereat. At the bracket 36, the end of a solid slide arm 45 is shown similarly pressfit at a bore 46 extending through the bracket 36. At generally the other side of the bracket 36, and shown in section, is the solid outward end of a mainly hollow sleeve 47, which is substantially identical to the other sleeve 41 and having an axial end bore 48 threadengaged by a screw fastener 49 that similarly extends through a bore 50 of the bracket 36 for engagement therebetween. Thus, brackets 35 and 36 rigidly are affixed to the housing-outward bored ends of the sleeve means 41 and 47 and the housing-outward ends of the slide arm means 39 and 45. The solid slide arms 39 and 45 are slidably supported through bushings 51 and 52, respectively, which bushings, in the exemplary embodiment, are pressfit through holes in the housing 27 of the cephalostat 10.

The sleeves 41 and 47, slidably extend through smooth openings 53 and 54, respectively, through the housing 27. It will be seen that the slide arm means 39 and 45, and the sleeves 41 and 47, are thereby slideably movable with regard to the housing 27. The interior of the housing 27 is generally shown at reference number 55 at a lower cavity portion thereof and at 56 at an upper cavity portion thereof. The lower cavity 55 accommodates the housing-inward telescoping portions of the movable sleeve means and slide arm means.

The relative motion of the sleeve means and slide arm means is provided by a gear and rack means 57 whereby to drivingly move the brackets 35 and 36 either away from, or toward, the housing 27. The gear and rack means 57 comprises a rotatable gear, or pinion, 58 having circumferential gear teeth 59 that engage opposingly faced gear racks 60 and 61. The gear racks 60 and 61 are respectively mounted to the sleeve means 41 and 47 by setscrew fasteners 62. The pinion 58 and gear racks 61 and 61 are, in the preferred embodiment, made of brass, which is well suited to accurate machining and has durability for long precise use for gearing assemblies. The pinion 58 is centrally bored at 63 for receipt therein of a shaft 64. A setscrew 65 secures the shaft to the pinion at a lower collar portion of the pinion generally shown at 66 in FIG. 4. An integrally cast intermediate horizontal wall 67 of the housing 27 separates the cavities 55 and 56 and includes a central opening 68 therethrough for the rotational receipt therein of the shaft 64. Atop the wall 67, and in movable relation thereto, a limit stop collar 69 is affixed by setscrew 70 to the shaft 64 whereby to prevent unwanted vertical displacement of the shaft. The shaft 64 extends upwardly through a central opening 71 of the top plate 33 and is joined to the top knob adjustment 26 of the assembly 25 whereby manual rotation thereof turns the pinion clockwise, or counterclockwise, as desired. The top plate 33 is removably secured to the housing 27 by machine screw fasteners 72 therebetween. A setscrew 73 secures the top knob adjustment 26 to the shaft 64 at a lower collar portion 74 of the knob 26. Thereby, it will be seen that rotation of the knob 26 turns the shaft 64 and the pinion 58 whereby to drive the gear racks 60 and 61 in opposite directions.

The sleeve 41 is generally tube-like and in the exemplary embodiment is hollow for a major portion of its length at a central passage 75 open at the housing-inward end and provided for the moving receipt therein of the solid slide arm 45. Correspondingly, the sleeve 47 has a central passage 76 extending also for a major portion of the length of the sleeve and having a housing-inward open end for the movable receipt therein of the opposingly directed solid slide arm 39. The lower end of the shaft 64 extends through a bottom plate 77 which is arranged under the downward open bottom of the cavity 55 of the housing 27 to close over the cavity 55, as best viewed in FIG. 4. In the embodiment disclosed, the lower end of the shaft 64 is pressfit through a collar 78, which is arranged beneath the plate 77. A setscrew fastening, or the like, may also be used for the attachment of the shaft 64 to the collar 78.

With reference to FIG. 4, it will be observed that the upper cavity 56 includes support apertures 79 for accommodation of the film cassette holder slide means 32 of the cassette holding adjustment assembly 28. Also, a slide adjustment means 80 for the nasion positioning assembly 11 is accommodated interiorly of the cavity 56. The lower cavity 55 is separated by the wall 67 and houses the movable sleeve means, slide arm means and gear and rack means of the adjustable assembly 25 in a convenient and compact arrangement with the cavity 55 and below cavity 56, whereby all said adjustment features are efficiently cooperative within the housing 27 as shown.

It will be appreciated that by the clockwise rotation of the knob adjustment 76, the pinion 58 will drive the gear racks 60 and 61 in opposite directions whereby to pull the brackets 35 and 36 toward one another. As the brackets move this way, the solid slide arms 45 and 39 associating with the sleeves 41 and 47, are caused to be further inserted interiorly of the hollow passages 75 and 76, respectively. A protective inward motion limit stop to the movement of the brackets 35 and 36 is preferably obtained by the ends of the sleeves 41 and 47 as they move toward abutments with the pressfit bushings 52 and 51. The limit stop is calculated in conjunction with the length of the gear racks 60, 61, so that at no time will the teeth 59 of pinion 58 leave gear-tooth engagement with the racks. The distance between the bushings 52, 51, and the ends of the associating sleeves 41, 47, respectively, is desirably provided to match the distance between the brackets 35 and 36, and the exterior of the housing 27 so that both conditions of abutment co-act as limit stops. Of course, just the abutment of the brackets 35, 36 with the housing 27 could provide the sole inward limit stop. The configurations for the earposts 12 and 13 may be variously formed whereby to be horizontally offset relative to the brackets 35 and 36 in order to dispose the plugs 14 and 15 at selected spacings from the brackets 35 and 36. Thereby the plugs 14, 15 can be horizontally offset as might be required and allow the ear brackets 35 and 36 to be snugly arranged against the side of the housing 27 during radiography, as shown for the offset configurations of brackets 35, 36 with regard to earposts 12, 13. Thus compactness and the reduction of protrusions are effectively achieved by the invention.

An outward motion limit stop is provided by, in preferred form, the provision of a setscrew fastener 81 extending transversely through an aperture 82 of the sleeve means 41 at a set distance from the smooth bore 53 of the housing 27 whereby upon rotating the top adjustment knob 26 in the counterclockwise direction, the screw fastener 81 moves with the sleeve means 41 toward the housing 27 and is stopped thereat by butting against the interior of the housing 27 adjacent the bore 53. This movement limit distance is set, similar to the inward motion limit stop, whereby the lengths of the gear racks 60 and 61 are sufficient to still be engaged with the pinion 58 when the setscrew fastener 81 contacts the housing 27 and thereby preventing the pinion teeth 59 from leaving gear-tooth contact with the racks and thus avoiding a disengagement of the gear and rack assembly 57.

In phantom lines, FIGS. 1-4 include an alternative form of the telescoping adjustment assembly 25 whereby it may be provided to be adjustable from below and to the rear of the cephalostat 10 rather than from above with the top adjustment knob 26. In this regard, therefore, the assembly 25 may be provided whereby to eliminate the top adjustment knob 26 and wherein the shaft 64 can be formed to stop at the plate 33, or extend upwardly therethrough to engage a rotatable collar, similar to the collar 78 at the plate 77, which would be similarly movable on the plate 33. The shaft 64 would also be provided with a limit stop collar 69 and be attached at the hub 66 of the pinion 58. A modification for this alternative of the assembly 25 is mainly provided generally at and below the bottom plate 77 wherein a larger collar 83 is replaces the smaller collar 78 and is affixed to the shaft 64 by a fastening means, such as a setscrew 84, thereby to also be rotatable with the shaft 64 under the plate 77. A radial bore 85 of the collar 83 receives therein a thread-engageable, or pressfit, pivot arm, or rod, 86 extending radially therefrom and outward of the rear of the housing 27 to be positioned generally rearwardly of the cephalostat 10, at the opposite side of the nasion assembly 11, best viewed in FIG. 4. At its opposite send, the pivot arm 86 includes a manual adjustment knob 87 to be gripped and rotated by the practitioner to create the same responsive motion of the gear rack assembly 57 that the top knob adjustment 26 imparts. As shown in FIG. 1, the pivot arm 86 and knob 87 project rearwardly of the cephalostat 10 in a conventional location to be also spaced away from the x-ray paths for both the tomographic x-ray assembly 17 of FIG. 1 and the fixed path of the lateral roentgenography arrangement shown in FIG. 2. The practitioner may simply move the pivot arm 86 in an arc to close and open the spacing between the earposts 12 and 13. The pivot arm 86, of course, may be made to be upwardly or downwardly inclined, or intermediately bent, as might be needed for use in a variety of cephalostat and head positioning device constructions and procedures. The top knob adjustment and the pivot arm adjustment forms of the invention are not intended thereby to be limited to use in the cephalostat 10.

Figure 6:
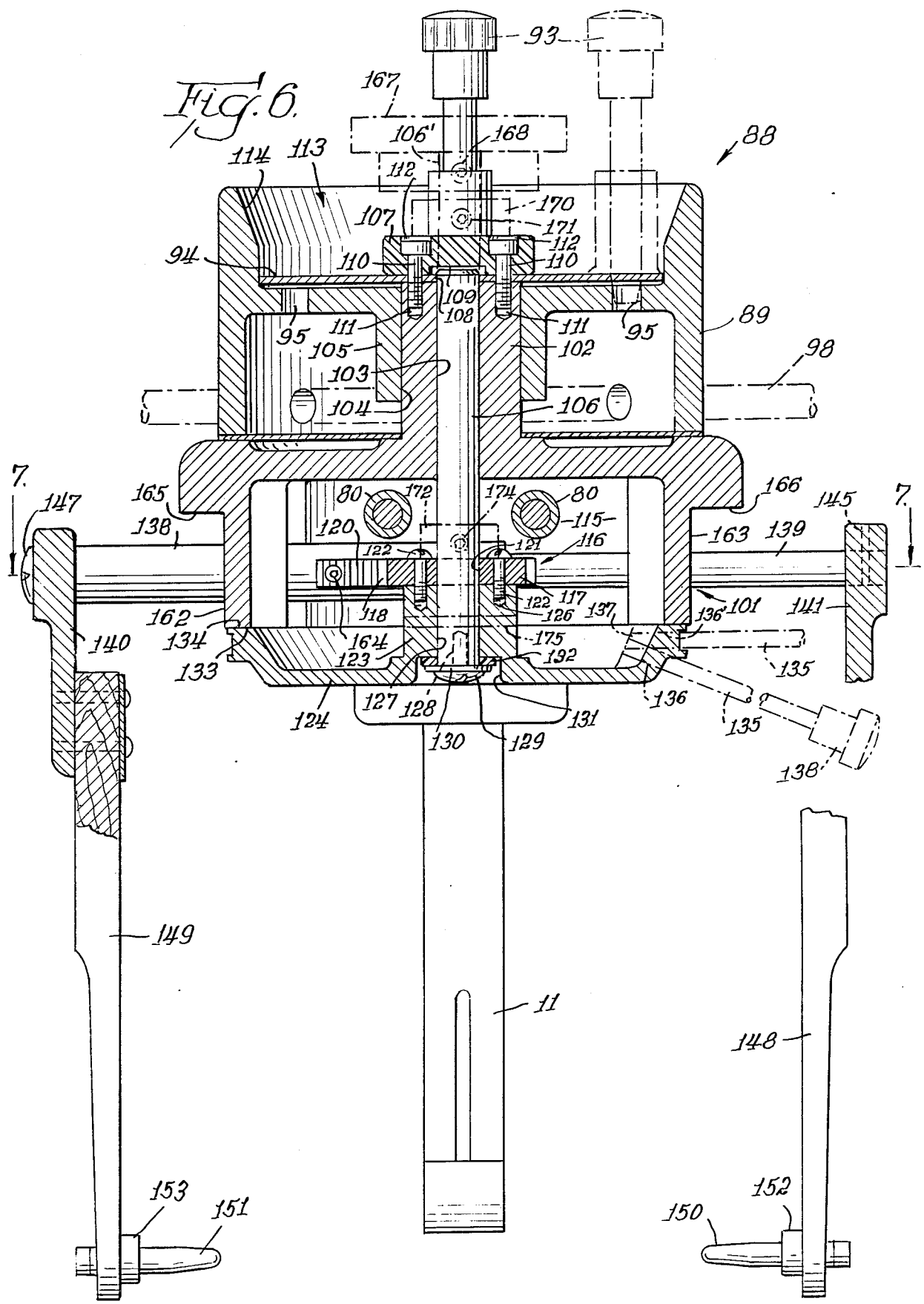
FIG. 6 is a vertical sectional view taken along line 6—6 of FIG. 5 showing the telescoping adjustment assembly accommodated interiorly of the cephalostat housing and the housing being mounted with a rotating bottom plate and an associating pivoting arm for movement of the telescoping assembly, and in phantom lines showing the top knob adjustment alternative for controlling the movement of the earpost, and wherein selectively insertable index pin means for rotationally adjusting the housings relative to each other is shown in a first position in solid lines, and in a second position in phantom lines.

Reference is now made to FIGS. 5-7, wherein a cephalostat 88 is shown for a type of device that is known in the industry as being rotationally or angularly adjustable to arrange the head at different angles relative to the x-ray source for the purposes of not merely making lateral cephalometric studies, but also making anterior, posterior, and oblique radiographs. An upper housing 89 of the cephalostat 88 is fixed and is associated with mounting means generally shown at 90 for attachment to a wall bracket 91. A lower housing 92 is rotationally adjustable relative to the upper housing 89 whereby to be able to rotationally position the patient's head therebelow at these different angular relationships relative to an x-ray tube (not shown). Both the housings 89 and 92 may be cast, preferably from aluminum or stainless steel, or they may be otherwise machined from metal slugs. The present invention of course has significant application for panoramic tomography due to the characterizing compact, non-protruding features virtually eliminating any outward projections for the head positioning means adjustment assembly. It should also be understood that the invention is equally beneficial for use in cephalometric studies for statically positioned x-ray tube radiography, as well as tomography, such also made possible by the cephalostat 10 of FIG. 2, and the rotational cephalostat 88 of FIG. 5 that allows for orienting the cranium, dentition, TMJ, etc. at various angles for either use with a fixed x-ray tube or with an axial tomographic rotating x-ray source. The cephalostat 88 has primary use in panoramic radiography wherein an adjustable cassette holding means, shown in phantom and discussed below, is deleted and a rotating tomographic x-ray assembly, such as assembly 17, is employed. Moreover, the invention renders both angularly adjustable and simple lateral-type cephalostats more efficient and precise by the tight sturdy-fitting telescoping sleeve and slide arm means and the nonprotruding features that advantageously allow for easier manipulation and accommodation of other apparatus, such as, nasion and orbitali positioners, cassette holders, indexing means for angular adjustments, various earpost shapes, and different housing configurations.

In FIGS. 5–7, phantom lines are used to denote alternative earpost configurations, optional cassette holding means for static x-ray tube radiography and adjustment means therefor, an optional orbitali positioner, and an alternative form of the adjustment means for the invention, as will be explained.

The angularly adjustable, rotational cephalostat 88 includes an indexing pin and collar means 93 extending through a cover plate 94 of the housing 89 whereby to be insertable into a plurality of indexing holes 95, which indexing means form no part of the present invention, but are shown to explain the adaptability of the invention to a variety of cephalostat devices, accessories, and features. The index pin and collar means 93 is shown by the solid lines to be in a standard lateral radiograph orientation at FIGS. 5 and 6, and in phantom lines in FIG. 6, following a 90° rotational adjustment of the lower housing 92 relative to the upper housing 89. The lower housing 92 is affixed to the top plate 94, as will be explained hereinafter, thereby the plate 94 is able to rotate relative to the stationary upper housing 89.

An orbitali positioning assembly 96 is mounted to the cephalostat 88 and is shown by phantom lines as an optional accessory. Similarly, a cassette holding assembly 97, having arms 98 slideably associating with the upper housing 89, is shown in phantom lines, and which is adjustable relative to the upper housing 89 and supported thereby so that as the lower housing 92 is placed in various angular relationships the holding assembly 97 may position a film cassette 99 therein enabling the desired angular radiograph to be made. The cephalostat 88 is, as stated, primarily useful for panoramic-tomography. Thus assembly 97 would be absent for the axial tomographic procedures, but is shown in phantom as an optional feature that may be added on or taken off the cephalostat 88 as needed.

A nasion positioning assembly 100 is may be optionally provided and functions in a conventional manner as does the nasion positioning assembly 11 shown for the cephalostat 10.

The cephalostat 88 cooperates with a telescoping adjustment assembly 101 in accord with the preferred embodiment of the invention. In a first form for use with the cephalostat 88, the adjustment assembly 101 is provided with a rear pivot rod, or arm, adjustment, and in a second form, in phantom lines, the assembly 101 is alternatively provided with a top knob adjustment, as will be explained hereinafter.

The bottom housing 92 includes a central upstanding hub 102 which is axially bored at 103, and is best understood with reference to the cross-sectional view of FIG. 6. The hub 102 is attached to the top plate 94 and rotates the plate 94 as the hub 102 turns within a smooth bore 104 that is made through a circumferentially surrounding collar 105 forming part of the upper housing 89. In the exemplary embodiment of said first form of the invention, a shaft 106 of the assembly 101 is pressfit within the bore 103 and is thereby rotational with the hub 102. At the upper end of the shaft 106, terminating generally at the top plate 94, a collar 107 is arranged to surround an aperture 108 through the top plate 94. The aperture 108 receives generally the upper end of the shaft 106 therethrough. A central recess 109 of the collar 107 accommodates the upper end of the shaft 106 extending from through the aperture 108. Screw fasteners 110 extend through the collar 107, which rests atop the plate 94, and pass through the plate 94 to thread-engage with the hub 102 at threaded holes 111 thereof. Thereby, the collar 107 is rigidly secured atop the top plate 94 whereby the hub 102, the plate 94 and the collar 107 are joined and secured to rotate together. The heads of the fasteners 110 are desirably counter-sunk at 112, or optionally may be made flush with the top surface of the collar 107. In the disclosed embodiment, the collar 107 is a hard plastic washer-like cap which can also offer a decorative appearance to the interior of the upper housing 89. It will be observed that the exposed upper portion of the housing 89 is a depressed well-like formation generally referenced at 113 having a peripheral conic tapering wall 114. In certain cephalostat devices, cone-like clutch plates are used in copperation with the walls 114 whereby to provide housing securement at selective angular relationships of the lower housing 92 relative to the upper housing 89 for positioning between those angular arrangements where indexing holes 95 are provided for the index pin and collar means 93. Typically the indexing holes 95 would be located at 45° increments. Therefore, a clutch plate releasably securable with the hub 102 and collar 107 could be tightened against the cone-like wall surfaces 114 and allow the practitioner to select intermediate angular relationships, i.e., 30°, 60°, etc.

The fixed shaft 106 extends downwardly through the bore 103 to emerge into an interior cavity 115 of the lower housing 92. Therein, the shaft 106 in the first form of the embodiment of the assembly 101 freely extends through a gear and rack assembly 116 of the telescoping adjustment assembly 101. The gear and rack assembly 116 includes a gear, or pinion, 117 having circumferential gear-teeth 118 engaged with opposing gear racks 119 and 120. In the exemplary embodiment of the first form of the assembly 101, at a central opening 121 of the pinion 117, the shaft 106 freely extends therethrough and the pinion 117 is thus rotatable about the shaft 106. The pinion 117 is attached by a plurality of screw fasteners 122 to a centrally bored hub 123 of a preferably integrally formed housing bottom plate 124. Smooth aperatures 125 are bored through pinion 117 to be aligned with threaded sockets 126 bored into the hub 123. The screw fasteners 122 pass through apertures 125 to be thread engaged within socket 126 and thus securing pinion 117 to bottom plate 124 at the hub 123 thereof. The plate 124 further includes a central through bore 127 that freely and rotatably receives therethrough the shaft 106. The shaft 106 terminates outwardly of the bore 127, as best viewed in FIG. 6, and includes an axial threaded end bore 128 for the thread-engagment with a screw fastener 129. A washer 130, preferably formed of steel, is interposed between the end of the shaft 106 and head of the screw fastener 129. The through bore 127 terminates, or opens, at the center of the plate 124 at a recess 131 whereby the screw fastener 129 and steel washer 130 are recessed from the bottom surface of the plate 124. In order to facilitate rotation of the plate 124 around the shaft 106, a fiber washer 132 is disposed between the steel washer 130 and the under surface of the plate 124 generally adjacent bore 127 and within recess 131. In this relationship, it will be therefore understood that rotation of the plate 124 is around the shaft 106, wherein plate 124 generally rotatably moves atop the fiber washer 132 supported by the washer 130 and the head of the fastener. Inasmuch as the pinion 117 is affixed to the hub 123 of the plate 124, it will be clear that the pinion 117 thereby may rotate clockwise or counter-clockwise responsively corresponding to the motion of the plate 124. The upper outward periphery of the plate 124 provides a meeting surface, or flat shoulder, 133 for smoothly meeting a lower outward flat bottom edge 134 of the sidewall of the lower housing 92 which generally defines the cavity 115 therewithin. Surfaces 133 and 134 are freely and relatively movable abutting surfaces permitting the rotating motion of the plate 124 relative to the housing 92.

In the first form of the exemplary embodiment, rotation of the plate 124 is achieved by the attachment of a pivot, arm, or rod 135 extending rearwardly of the cephalostat 88 and engaged to the plate 124, as shown by the thread-engaging of an end thereof into a threaded hole 136 of the plate 124. An increased wall thickness at boss 137 is provided on plate 124 at the location of the hole 136 to facilitate sturdy engagement with the pivot arm 135 whereby the thickness of the plate 124 is thereby enlarged for reinforcement and support of the arm 135 within the hole 136. The pivot arm 135 optionally may be made to be pressfit into a non-threaded hole 136. However, thread engagement is preferred since it allows for the facile removability of the pivot arm 135. The pivot arm 135 terminates outwardly of the cephalostat 88 at a knob 138 facilitating manual adjustment by the practitioner grasping the knob 138 and moving the pivot arm 134 to rotate the plate 124. An alternate bore 136' may be horizontally formed wherein the pivot rod 135 would reside in a horizontal plane rather than in the preferred downwardly inclined disposition shown in FIG. 6. Optionally, both bores 136 and 136' may be provided through the plate 124 to give the practitioner a selection in the orientation of the pivot rod 135. A common interior opening of the dual bores 136 and 136' through boss 137 would be shared, as would be understandable to one skilled in the machining arts in view of FIG. 6.

The operation of the telescoping adjustment assembly 101 is achieved by the physician facilely grasping the knob 138 at the end of pivot rod 135 and pushing the knob 138 in an arc to rotate the plate 124. Thereby, the pinion 117 will be responsively turned since the hub 123 of the plate 124 is affixed to the pinion 117.

The opposing gear racks 119 and 120 are operated by the pinion 117 at the gear and rack assembly 116 substantially the same as the gear and a rack assembly 57 of the telscoping adjustment assembly 25, and alternative form, as shown in FIGS. 1–4. The assembly 116 serves to move a reciprocating sleeve and slide arm means substantially identical to assembly 57. Specifically, the gear rack 119 is affixed to a tube-like sleeve 136 which movingly receives into an open end hollow passageway a solid slide arm 137 at a housing-inward end thereof. The opposite gear rack 120 is carried on a tube-like sleeve 138 which also movingly receives a solid slide arm 139 into an open end hollow passageway, at a housing-inward end thereof, as would be understood. Housing-outward ends of the slide arms 137 and 139 are pressfit into opposing brackets 140, 141, respectively, at bracket bores 142, 143, and may be further secured by pin fasteners 144, 145 extending downwardly through the brackets into aligned transverse bores drilled into the slide arms, as shown in FIG. 6. Housing-outward ends at the sleeve means 136 and 138, are attached to the brackets 140 and 141 by screw fasteners 146 and 147, respectively, which engage threaded axial end bores of the sleeve means 136 and 138, respectively, after passing through smooth bores drilled through the brackets, in the same fashion as shown for the sleeves and brackets of the assembly 25, best viewed in FIG. 3. Earposts 148 and 149 extend downwardly from, and are supportably carried by, brackets 141 and 140, respectively. Earposts 148 and 149 are substantially identical to earposts 12 and 13 shown in FIGS. 1–4. At their lower ends, ear plugs 150 and 151 are attached by attachment assemblies 152 and 153, respectively, in similar fashion to the attachments 37 and 38 for earplugs 14 and 15 to earposts 12 and 13 described in conjunction with the embodiments of FIGS. 1–4. As an alternative, an earpost 148' is shown in phantom lines in one of many other possible shapes for the earposts and having a generally block-"C" shape. This particular "C" shape thereby eliminates a vertical member immediately adjacent the side of the patient's head, which can be helpful such as for close radiographic study of the TMJ, for example. In preferred form, the earposts 148 and 148' are non-metallic and could be made of wood or plastic to prevent clouding or shadowing of the x-ray. The use of the block-"C" shaped earpost 148', or the like, may also be useful with respect to a panoramic tomographic procedure wherein it is usually desirable to eliminate as many physical obstructions from adjacent the side of the head as possible, particularly when TMJ roentgenography in undertaken. Accordingly, the invention easily allows for removing or displacing accessories and head positioning adjusting means from the moving path of the x-ray tube and film, as is desirable in axial tomographic procedures. For tomographic use, the cassette holding means 97 would be removed from the cephalostat 88 and, for example, an x-ray assembly, such as assembly 117 shown in FIG. 1 could be utilized to rotate about the patient's head, which is positioned by the cephalostat 88.

As in the assembly 25, the assembly 101 provides for the earplugs 150 and 151 to position the porion axis therebetween whereby radiographs for cephalometric studies may be taken over time with assurance that the patient's head is re-aligned by the cephalostat 88 in the same orientation with respect to the x-ray source and film each time a cephalometric series is taken. Correspondingly, the mid-sagital and Frankfort planes are helped to be placed in the appropriate position by the further cooperation of the nasion positioner 100, and the optional orbitali positioner 96 may be utilized to establish the proper positioning of the eye socket. Then, the positioning means 98 of the cassette holder assembly 97 can be adjusted to dispose the film 99 at a selected distance from the mid-sagital plane, as would be understood.

In the quick and efficient operation of the adjustment assembly 101, the practitioner may arrange the earposts 148 and 149 to be spaced away from the housing 92 by grasping and then pushing the turn knob 138 counterclockwise thereby urging pivot rod 135 to rotate plate 124 and in turn thereby rotating the pinion 117, as viewed in FIG. 7, in a counter-clockwise direction to drive the gear racks 119 and 120 toward the walls of housing 92, generally referenced at 154 and 155, respectively. At the walls 154 and 155, the sleeve means 136 and 138 are freely slideable through smooth bores 156 and 157, respectively, drilled therethrough in similar fashion to the bores 54 and 54 through the housing 27 for the assembly 25. The slidable motion of the slide arms 137 and 139 is made possible by the provision of bushings 158 and 159, respectively, fitted through bores in wall portions 160 and 161, respectively, of the lower housing 92. The bushings 158 and 159 essentially serve the same slide and support function for the slide arms as bushings 51 and 52 of the telescoping adjustment assembly 25.

The inward motion limit stop for the gear and rack assembly 116 is provided by the abutment of the brackets 140 and 141 with flattened exterior walls 162, 163, respectively, at opposite lateral sides of the lower housing 92. A second, or cooperative, inward motion limit stop is provided by the interior of the wall portions 160 and 161 which will stop the movement of the sleeves 136 and 138, respectively, when moved to be abutted against them. The inward motion limit stops provided by the outside flat walls 162 and 163, and the walls 160 and 161 for the brackets and the sleeves, stop the gear and rack assembly 116 so that the pinion 117 cannot be overturned and will always be maintained in gear-tooth engagement with the racks 119 and 120 so that disengagement is prevented. As with the telescoping adjustment assembly 25, the gear racks 119 and 120 are preferably screw-attached to the sleeve means, shown at setscrew fasteners 164, for the affixation of the gear rack 120 to the sleeve 138 and the gear rack 119 to the sleeve 136. A preferable plurality of four fasteners 110 attach the collar 107 to the hub 102, and a preferable plurality of four fasteners 122 secure the pinion 117 to the hub 123. The fastenings are symmetrically arranged. The invention is not considered to be limited by this number, and four fastening locations for each are illustrated merely for the purposes of explaining the exemplary embodiment of the preferred form of the invention.

As for the telescoping adjustment assembly 25, the material envisioned for gear pinion 117 and gear racks 119 and 120 is brass due to its durability and capability of accurate machining.

The location of the handle 138 and pivot rod 135 is preferably behind the housing 92 to be away from interfering with the radiographic process similar to the arrangement of knob 87 and pivot rod 86, as shown in the alternative embodiment and best depicted in phantom lines in FIG. 4. In both the embodiments shown in FIG. 4, and in FIGS. 5-7, the pivoting rods may be horizontal, or inclined upwardly or downwardly, depending upon the space requirements for the type of radiography or tomography employed, or as might be needed to suit particular preferences. This capability of providing a variety of pivot rod conformations, along with the ability for modification of the shapes of the earposts, such as 148 or 148', allows the practitioner to be able to specify certain apparatus arrangements as needed to efficiently position the patient for particular roentgengraphic requirements. The capabilities of the invention to aid in accurately positioning the porion axis, midsagital, Frankfort plane, etc., and to facilitate making the specified roentgenograph with virtually no protuberances extending outwardly of the cephalostat, are great benefits and improvements in cephalometric radiography. In furtherance of these goals, it will be seen that the side of housing 92 may include a bracket-complementary recesses, generally denoted at 165 and 166, at opposite sides of the cephalostat 88, so that the brackets 140 and 141 may nestingly be accommodated against the flattened sidewalls 162 and, beneath these recesses 165 and 166, facilitating even further compactness as seen in FIGS. 5 and 6, when the earplugs 150 and 151 are in position inside the ear canals. The recesses 165 and 166 are shoulder-like indents on the housing spaced inward about the same dimension as the bracket thicknesses in order to achieve this compact, trimline configuration, for lateral, anterior/posterior and oblique positioning for fixed tube radiography, or for axial tomography.

The telescoping adjustment assembly 101 is further adaptable to being provided with a top knob adjustment arrangement in an alternate form of the invention. Shown in phantom lines in FIGS. 5-7, the cephalostat 88 is provided with a top knob adjustment 167 for rotation of the shaft 106. A setscrew 168 attaches the top knob adjustment 167 to an extended length of the shaft 106 generally shown at 106'. The collar 107 is alternatively thereby formed to have a through bore 169 for receipt therethrough of the extended length 106'. For this form of the invention, the shaft 106 is vertically supported above collar 107 by an added collar 170 having a plurality of setscrews 171 attaching the collar 170 to the extension 106'. The collar 170 freely rotates atop collar 107 and provides a downward axial limit stop for shaft 106. The shaft 106 is made in this alternate embodiment with a slightly smaller diameter than the bore 103 whereby to be rotatable therein upon turning top adjustment knob 167, instead of being statically pressfit therein, as shown for the pivot rod adjustment 135. The pinion 117 is modified to be provided with an upstanding hub 172 that is axially bored at 173 for receiving the shaft 106 therethrough. The hub 172 is affixed to shaft 106 by means of at least one setscrew 174. Thereby, the pinion 117 is affixed to the shaft 106 for rotation responsive to the rotation of top adjustment knob 167. The screw fasteners 122 preferably would be eliminated since the shaft 106, not the bottom plate 124, is relied upon for rotation of the pinion 117 in this form of the invention. The plate 124, in the preferred embodiment of this alternate form of the invention, is locked through the hub 123 thereat by a pin 175 extending transversely through a bore drilled through the shaft 106 and the hub 123. Thereby the shaft 106 rotates the plate 124 and pinion 117 as a joined unit with the top knob adjustment 167, as best understood in view of FIG. 6. The shaft 106 remains axially engaged by a screw fastener 129 at its lower end, which also includes the steel washer 130. The fiber washer 132 would be preferably eliminated in this top knob adjustment alternative, inasmuch as the plate 124 is provided to rotate with the rotating shaft 106, and not around a static shaft 106 as in the pivot arm adjustment first embodiment. Optionally, the location of the fiber washer 132 could be taken by a shake-proof type washer, or a serrated frictional surface could be provided atop steel washer 130, whereby the pin 175 might then be eliminated and the frictional connection made possible by fastener 129 bearing upward against such a shake-proof washer, or by serrated surface, would keep plate 124 secured to the shaft 106 to be rotatable therewith. The pinion 117 is prevented from downward vertical displacement be being downwardly limit-stopped by the collar 170 attached to the shaft 106 to rotatably abut atop the collar 107. Upward vertical displacement of the pinion 117 is prevented by the plate 124 at its peripheral edge 133 abutting against housing surface edge 134, which prevents the shaft 106 from displacing axially upward because the washer 130 is held by the fastener 129 to bear against the plate 124 in recess 131. Thus, accurate alignment and constant engagement of the pinion 117 with the gear racks 119 and 120 are maintained. For the top knob adjustment alternative, the pivot rod 135 would, of course, not be required, but could optionally be included whereby to provide a dual adjustment means for assembly 101 since plate 124 still rotates with pinion 117 in the second form of the invention.

It would be further understood, with conjunctive reference to FIG. 4, that in accord with the top knob adjustment and gear and rack assembly as described in our co-pending application Ser. No. 865,250, filed May 19, 1986, and particularly as shown in FIG. 5 thereof, assembly 101 herein might be modified for a top knob adjustment alternative embodiment having a freely turning shaft 106 by optionally making the plate 124 a simple flat and fixed cover plate, such as plate 77 of FIG. 4, and eliminating the central hub 123. In this form of the invention the shaft 106 could terminate substantially at the connection to the pinion 117. The gear hub 172 would be similarly affixed to the shaft 106 as by the setscrew fasteners 174 to be rotatable therewith. In order to assure an axial limit stop so that the pinion 117 does not disengage from the gear racks 119 and 120, a collar formed like the collar 170, or similar to collar 50 of our said co-pending application, could be secured along the shaft 106 to rotatably abut against the housing 92 above pinion 117 and generally at the bottom of the axial bore 103. This interposed limit collar would create an upward axial motion limit stop acting in cooperation with the downward axial motion limit stop provided by the collar 170 similar to upper collar 56 of our said co-pending application, to likewise prevent vertical axial displacement of the pinion. Accordingly, the plate 124 might simply be provided in a simple flat configuration as found with bottom plate 77 shown in FIG. 4, or plate 41 of our said co-pending application.

In further regard to FIG. 4, a modification to the top knob adjustment assembly might be made wherein the bottom collar 78 could be placed inwardly of cavity 55 generally above plate 77, and the shaft 64 shortened accordingly to terminate within the cavity 55 having the collar 78 secured to the shaft 64 below the collar 66 of the pinion 58. In this arrangement, the collar 78 could have a thickness spanning the distance between plate 77 and collar 66 to provide an axial limit stop and maintain the pinion 58 in engagement with the gear racks 60 and 61. Such modification would be applicable to the top knob adjustment form of the assembly 101 at the lower end of the shaft 106 by modifying, as previously suggested, the plate 124 to be generally flat such as at 77 of FIG. 4, or plate 41 of said co-pending application, and interposing a collar between the plate 24 and the pinion 117.

It should be understood that the invention is not limited to the disposition of a gear and rack assembly, telescoping sleeve means and slide arm means to be in a horizontal plane. It is envisioned, for example, that a vertically arranged pinion may be engaged to gear racks above and below the pinion which reside in substantially a vertical, rather than horizontal, plane. Accordingly, a knob adjustment, instead of being a top knob adjustment, might be a side knob adjustment connected to a horizontal shaft extending from the pinion. The side knob adjustment could also be mounted at the exterior of a housing and outwardly of a cephalostat. Likewise, a pivot arm, or rotatable plate, could be provided at the exterior side of a cephalostat to be rotatable in generally a vertical, rather than horizontal, plane for driving a vertically oriented pinion and associated vertically coplanar gear racks, telescoping sleeve means and slide arm means. For the vertically co-planar arrangement of the sleeve means and slide arm means, the earposts would be appropriately mounted on earpost brackets and extend therefrom in a substantially similar manner as those shown in the drawings.

Additionally, the invention is not limited to sleeve means and insertable slide arm means that are both circular in cross-section. It is envisioned that complementarily shaped, or telescope-capable, geometric configurations may be utilized for the sleeve means and slide arm means, such as square shaped slide arm means and a complementary box-shaped sleeve means sized to slide-accommodate the square slide arm shape. Additionally, oval shapes, triangle shapes, other polygonal shapes, and the like, may be utilized wherein the exterior shape of the slide arm means is slide-insertable for telescoping within the interior passage of the sleeve means. Further, the cross sectional shapes of the slide arm means and sleeve means need not be geometrically defined as similar. Geometrically "similar" means in this context the same shape, i.e., both square, but different in size or position. For example, a cross-sectionally circular sleeve can be engageable by a cross-sectionally triangular slide arm means approximately sized to fit therein. In all forms of the invention the slide insertability of the slide arm means for telescoping within the sleeve means is preferably achieved by a close size fitting therebetween which desirably achieves a very stable unwobbly assembly also due to the relatively long telescoping overlap capable of being made between them, rather than a mere connection at ends thereof, or the supportive slide-through of an arm through a slide bore of a bracket, as in the prior art.

It therefore can be appreciated that a telescoping adjustment assembly for a cephalostat is provided that offers a compact and very accurate, stable adjustment primarily useful for the earposts and ear plug means for positioning the head, and the porion axis defined between the ear canals, for the proper alignment thereof in cephalostat. In the embodiments disclosed, the adjustment may be made by means of an adjustment knob connected to a shaft extending from a pinion, or by a plate connected to the pinion for movement by a laterally extending pivot arm, or by various modifications of the pinion rotating means. The invention is not to be considered to be limited to the disclosed means for turning the gear and rack for the unique telescoping adjustment assembly.

What is claimed is:

1. A telescoping adjustment assembly for head positioning means in a cephalostat, said telescoping adjustment assembly comprising:
   a rotatable pinion;
   a pair of opposingly faced gear racks being engaged by said pinion, the gear racks being mounted in substantially parallel relationship on a pair of sleeve means, whereby upon rotation of the pinion said gear racks, and thereby said sleeve means, are carried in generally opposite directions;

said sleeve means having two ends, a hollow passageway therein, one end of which being an open end of the passageway and the other end being attached to a bracket means for supporting head positioning means thereon;

a pair of slide arm means having an end thereof slidably accommodated within said hollow passageway of said sleeve means through said open end of the sleeve means and said slide arm means having an opposite end thereof being attached to said bracket means;

a cephalostat having a housing means;

said sleeve means and slide arm means slideably and supportably mounted to said cephalostat housing means whereby upon rotation of the pinion said bracket means are adjustably movable relative to the cephalostat housing means; and, means for rotating said pinion, said means being manually rotatable for moving said bracket means.

2. A telescoping adjustment assembly as claimed in claim 1 wherein head positioning means are carried by said bracket means and comprise earposts connected thereat at one end thereof and having an opposite end supportably carrying ear plug means thereat for insertion into a patient's ears for positioning the person relative to a cephalostat.

3. A telescoping adjustment assembly as in claim 1 wherein said pinion and gear racks are made of metal.

4. A telescoping adjustment assembly as in claim 3 wherein said pinion and gear racks are made of brass.

5. A telescoping adjustment assembly as in claim 1 wherein said assembly includes limit stop means whereby to prevent disengagement of the pinion with the gear racks.

6. A telescoping adjustment assembly as claimed in claim 1 wherein said sleeve means are metal generally tube-like members having said hollow passageway extending therein for a major portion of the length thereof.

7. A telescoping adjustment assembly as claimed in claim 1 wherein said slide arm means are substantially solid arms.

8. A telescoping adjustment assembly as claimed in claim 1 wherein the ends of said sleeve means attached to said bracket means are attached thereto by mechanical fasteners therebetween.

9. A telescoping adjustment assembly as claimed in claim 1 wherein said means for rotating said pinion is extends outwardly of the cephalostat housing means.

10. A telescoping adjustment assembly as claimed in claim 1 wherein the end of said slide arm means attached to said bracket means is attached by mechanical fastening comprising pressfitting said end of the slide arm means within an aperture of said bracket means.

11. A telescoping adjustment assembly as claimed in claim 1 wherein said pinion, gear racks, sleeve means, and slide arm means are comprised of metal.

12. A telescoping adjustment assembly as claimed in claim 1 wherein said pinion, gear racks, and open end of said sleeve means for the slidable accommodation of said one end of said slide arm means, are accommodated interiorly of the cephalostat housing means.

13. A telescoping adjustment assembly as claimed in claim 1 wherein said assembly includes slidable support means mounted to the cephalostat housing means to provide the slideable support of said slide arm means therethrough and comprising bushing means accommodated within a bore through the wall of a cephalostat housing means.

14. A telescoping adjustment assembly as in claim 1 wherein said assembly is provided in a cephalostat for lateral roentgenography.

15. A telescoping adjustment assembly as claimed in claim 1 wherein said assembly is provided in an adjustable housing means of a cephalostat of the type capable of adjustably positioning the patient's head for lateral, posterior, anterior and oblique radiographs.

16. A telescoping adjustment assembly as claimed in claim 1 wherein said assembly is provided in a cephalostat for panoramic tomography.

17. A telescoping adjustment assembly as claimed in claim 1 wherein said bracket means support head positioning means comprising earposts having ear plug means thereon for insertion into the ears of the patient whereby to align the porion axis therebetween.

18. A telescoping adjustment assembly as claimed in claim 1 wherein said bracket means are movable in opposite directions upon the rotation of said pinion and are spaced substantially equi-distantly from the center of said pinion at all times.

19. A telescoping adjustment assembly as claimed in claim 1 wherein at the ends of said sleeve means and slide arm means being attached to said bracket means substantially no parts of said sleeve means and slide arm means extend outwardly from the pinion-opposite side of said bracket means whereby to provide a compact assembly particularly beneficial for tomographic radiography.

20. A telescoping adjustment assembly as claimed in claim 1 wherein said means for rotating the pinion includes a rotatable shaft means extending from the pinion whereby to be capable of rotating said pinion thereby being capable of moving said gear racks and said bracket means.

21. A telescoping adjustment assembly as claimed in claim 20 when said shaft means terminates at a knob adjustment means capable of being manually rotated.

22. A telescoping adjustment assembly as claimed in claim 1 wherein said means for rotating said pinion comprises a plate means capable of being mounted on a cepahlostat housing and having a hub portion thereof rotatably arranged with said pinion whereby to be capable of rotating said pinion upon rotating said plate means.

23. A telescoping adjustment assembly as claimed in claim 22 wherein said plate means associates with a pivot arm means attached thereto whereby said pivot arm means may be manually moved to thereby rotate said plate means and correspondingly rotate said pinion.

24. A telescoping adjustment assembly as claimed in claim 1 wherein said means for rotating said pinion comprises a rotatable shaft means axially engaged therewith.

25. A telescoping adjustment assembly as claimed in claim 24 wherein said shaft means includes stop collar means cooperative with the cephalostat housing means whereby to prevent said shaft from becoming axially displaced and thereby preventing disengagement of the pinion from said gear racks.

26. A telescoping adjustment assembly for head positioning means in a cephalostat, said assembly comprising a gear and rack assembly movably supported interiorly of a cephalostat housing and comprising a gear drivingly engaged to a pair of opposing gear rack means wherein the gear is rotatable to oppositely move the gear rack means upon the rotation thereof;

sleeve means carrying the rack means whereby upon rotation of said gear said sleeve means move in opposite directions;

said sleeve means being substantially tubular for a major portion thereof and being open ended at least at one end thereof whereby to be capable of slidably receiving slide arm means through the open end and thereby within the tubular portion;

slide arm means having opposite ends, one end being slidably accommodated within said sleeve means tubular portion;

said slide arm means and sleeve means being slidably cooperative at said ends thereof interiorly of said cephalostat housing and said sleeve means and slide arm means having housing-outward ends affixed to bracket means, said sleeve means and slide arm means supportably carrying said bracket means relative to said housing in response to the rotation of said gear;

said cephalostat housing including means for slidably receiving said sleeve means and slide arm means therethrough whereby said sleeve means and slide arm means are freely movable so that said bracket means may be carried correspondingly thereby; and, said bracket means capable of movably supporting head positioning means for use in positioning a person's head.

27. A telescoping adjustment assembly as claimed in claim 26 wherein said gear is supported by rotating means having a manual operable portion thereof arranged outwardly of said cephalostat housing.

28. A telescoping adjustment assembly as claimed in claim 27 wherein said rotating means comprises a shaft extending axially from said gear and said manually operable portion comprising a rotatable adjustment knob means.

29. A telescoping adjustment assembly as claimed in claim 27 wherein said rotating means comprises a rotatable plate means arranged with said housing and having a portion thereof capable of being rotatably arranged with said gear and having means extending outward of said housing and capable of manually being operated exteriorly of said cephalostat housing whereby to rotate said gear.

30. A telescoping adjustment assembly as claimed in claim 26 wherein said cephalostat housing is a one-position cephalostat being non-angularly adjustable.

31. A telescoping adjustment assembly as claimed in claim 26 wherein said cephalostat housing includes two portions, one being rotatable relative to a second.

32. A telescoping adjustment assembly as claimed in claim 26 wherein said housing-outward ends of said sleeve means and slide arm means are attached to said bracket means whereby substantially no portions thereof extend outwardly of said bracket means.

33. A telescoping adjustment assembly as claimed in claim 26 wherein the housing has generally complementarily shaped wall recess means adapted to nest said bracket means thereat whereby to compactly accommodate said bracket means against said housing.

34. In a cephalostat for use with a tomographic x-ray assembly, a telescoping adjustment assembly for head positioning means, said telescoping adjustment assembly comprising:

sleeve means affixed to opposingly faced gear racks, said gear racks being oppositely driven by a pinion being gear-tooth engaged therebetween and being rotatable whereby to move said sleeve means in opposite directions, said sleeve means being generally tubular having open ends at first ends of each opening to a passageway therein and opposite second ends being secured to bracket means, said bracket means being movably carried by said sleeve means upon rotation of the pinion, each said bracket means further being secured to one end of a slide arm means, an opposite end of said slide arm means being insertably engageable with a sleeve means through said open first end thereof whereby upon the movement of said sleeve means each said slide arm means is oppositely directed with respect to the respectively engaged sleeve means wherein said bracket means are thereby movable toward or away from a patient's head corresponding to the rotation of said pinion.

35. A telescoping adjustment assembly for the head positioning means of a cephalostat for fixed x-ray tube roentgenography, said assembly comprising:

sleeve means affixed to opposingly faced gear racks, said gear racks being oppositely driven by a pinion being gear-tooth engaged therebetween and being rotatable whereby to move said sleeve means in opposite directions, said sleeve means being generally tubular having open ends at first ends of each opening to a passageway therein and opposite second ends being secured to bracket means, said bracket means being movably carried by said sleeve means upon rotation of the pinion, each said bracket means further being secured to one end of a slide arm means, an opposite end of said slide arm means being insertably engageable with a sleeve means through said open first end thereof whereby upon the movement of said sleeve means each said slide arm means is oppositely directed with respect to the respectively engaged sleeve means wherein said bracket means are thereby movable toward or away from a patient's head corresponding to the rotation of said pinion.

36. A telescoping adjustment assembly for head positioning means of an angularly adjustable cephalostat capable of adjustably positioning the patient's head for lateral, anterior, posterior, or oblique, radiographs, said assembly comprising:

sleeve means affixed to opposingly faced gear racks, said gear racks being oppositely driven by a pinion being gear-tooth engaged therebetween and being rotatable whereby to move said sleeve means in opposite directions, said sleeve means being generally tubular having open ends at first ends of each opening to a passageway therein and opposite second ends being secured to bracket means, said bracket means being movably carried by said sleeve means upon rotation of the pinion, each said bracket means further being secured to one end of a slide arm means, an opposite end of said slide arm means being insertably engageable with a sleeve means through said open first end thereof whereby upon the movement of said sleeve means each said slide arm means is oppositely directed with respect to the respectively engaged sleeve means wherein said bracket means are thereby movable toward or away from a patient's head corresponding to the rotation of said pinion.

* * * * *

UNITED STATES PATENT AND TRADEMARK OFFICE
CERTIFICATE OF CORRECTION

PATENT NO. : 4,759,361
DATED : July 26, 1988
INVENTOR(S) : James L. Gallop and Andrew J. Majka It is certified that error appears in the above-identified patent and that said Letters Patent are hereby corrected as shown below:

Col. 2, Line 49 delete the misspelling "ide" and insert therefor --slide--.

Col. 7, Line 67 delete "threadengaged" and insert therefor --thread-engaged--.

Col. 15, Line 8 immediately after the word "bores" delete the number "54" and insert therefor --53--.

Signed and Sealed this

Twenty-eighth Day of February, 1989

*Attest:*

DONALD J. QUIGG

*Attesting Officer*  *Commissioner of Patents and Trademarks*